United States Patent
Greene et al.

(10) Patent No.: US 6,316,182 B1
(45) Date of Patent: Nov. 13, 2001

(54) DETECTION OF REVERSE TRANSCRIPTASE BY DNA HYBRIDIZATION ASSAY

(75) Inventors: Richard Alfred Greene, Westford; Gerald Jospeh Litt, Wellesley, both of MA (US)

(73) Assignee: Nen Life Science Products, Inc., Boston, MA (US)

(*) Notice: Subject to any disclaimer, the term of this patent is extended or adjusted under 35 U.S.C. 154(b) by 0 days.

(21) Appl. No.: 07/913,121

(22) Filed: Jul. 14, 1992

Related U.S. Application Data (63) Continuation-in-part of application No. 07/821,512, filed on Jan. 15, 1992, now abandoned.

(51) Int. Cl.⁷ .............. C12Q 1/68; C12Q 1/48; C12P 19/34
(52) U.S. Cl. .............. 435/5; 435/6; 435/91.2; 435/91.51; 435/91.1; 435/15
(58) Field of Search .............. 435/6, 5, 91, 91.5, 435/91.51, 91.2, 91.1, 15; 935/77, 78, 82, 18

(56) References Cited

U.S. PATENT DOCUMENTS

| | | | |
|---|---|---|---|
| 5,021,335 | 6/1991 | Tecott et al. | 435/6 |
| 5,413,906 * | 5/1995 | Eberle et al. | 435/5 |

FOREIGN PATENT DOCUMENTS

| | | |
|---|---|---|
| 0187041 | 9/1986 | (EP) . |
| 0272098 | 6/1988 | (EP) . |
| 0392459 | 10/1990 | (EP) . |
| 0443823 | 8/1991 | (EP) . |
| 3-53880 | 3/1991 | (JP) . |
| 9006044 * | 6/1990 | (WO) . |
| 9204467 | 3/1992 | (WO) . |

OTHER PUBLICATIONS

Abstract, Greene et al., "A Non–Isotopic Assay For Measurement of Reverse Transcriptase Activity", A World United Against AIDS Conference, Jul. 19–24, 1992.

Abstract, Eberle et al., "Reverse Transcriptase Activity Measured By ELISA", M.A. 1084, p. 113 Jun. 1991.

Abstract, Konig et al., "A Highly Sensitive Non–Radioactive Microassay For HIV–1 Reverse Transcriptase", Keystone Symposia Conference, Mar. 27 to Apr. 4, 1992, p. 36.

Josef et al., "Reverse Transcriptase Activity Measured by ELISA," VII International Conference on AIDS, Florence, Jun. 16–21, 1991, vol. 1; Conf 7; Abstract.

Milavetz et al. "Reverse transcription, a Probe by the Immobilized Template Poly (adenylic acide)–Agarose," Molecular Pharmacology, vol. 13, 1977, New York, pp. 496–503.

Krug et al., Method in Enzymology, vol. 152, pp. 316–325 (1987). "First Strand cDNASynthesis Primed with Oligo(dT)".

Du Pont Literature (Sep. 1991).

(List continued on next page.)

*Primary Examiner*—Carla J. Myers
(74) *Attorney, Agent, or Firm*—Gifford, Krass, Groh, Sprinkle, Anderson & Citkowski, P.C.

(57) ABSTRACT

A method for detecting reverse transcriptase (RT), utilizing RT-catalyzed generation of cDNA complementary to an RNA template and detecting cDNA in a DNA hybridization reaction, is provided. Also provided is a method for detecting and/or quantitating drug resistance of reverse transcriptase in a sample and a method for evaluating ability of a compound to inhibit reverse transcriptase activity.

7 Claims, 1 Drawing Sheet

OTHER PUBLICATIONS

Myers et al., 'Thermostable Reverse Transcriptase/DNA Polymerase', Cetus Corporation, Perkin–Elmer Cetus, amplifications: A Form for PCR Users, Oct. 1991, Issue 7, pp. 5–6.

Mogensen Exp Cell Res (1991) 196: 92–98.*

Goff et al., J. Acq Immune Defie Syndromes 1990 3 : 817–831.*

Konig et al, J. Cell Biochem, 1992, Supplement 16E, Abstract Q 222, p. 36.*

Laquel Biochem Biophys Acta 1990 1048 :139–148.*

Urdea Nucl Acids Res (1988) 16: 4937–4956.*

* cited by examiner

FIG-1

SEQUENCE LISTING (1) GENERAL INFORMATION:

(iii) NUMBER OF SEQUENCES:12

(2) INFORMATION FOR SEQ ID NO:1:

(i) SEQUENCE CHARACTERISTICS:
      (A) LENGTH:89 bases       (B) TYPE:nucleic acid       (C) STRANDEDNESS:single stranded       (D) TOPOLOGY:linear    (ix) FEATURE:
      (A) NAME/KEY:Portion of multiple cloning site from plasmid
         pSP72
      (D) OTHER INFORMATION:

(ix) SEQUENCE DESCRIPTION:SEQ ID NO:1:

GGGAGACCGG CAGAUCUGAU AUCAUCGAUG AAUUCGAGCU CGGUACCCGG GGAUCCUCUA    60

GAGUCGACCU GCAGGCAUGC AAGCUUCAG    89

(2) INFORMATION FOR SEQ ID NO:2:

(i) SEQUENCE CHARACTERISTICS:
        (A) LENGTH:89 bases         (B) TYPE:nucleic acid         (C) STRANDEDNESS:single stranded         (D) TOPOLOGY:linear     (ix) FEATURE:
        (A) NAME/KEY:RNA Template         (D) OTHER INFORMATION:

(ix) SEQUENCE DESCRIPTION:SEQ ID NO:2:

```
GACUUCGAAC GUACGGACGU CCAGCUGAGA UCUCCUAGGG GCCCAUGGCU CGAGCUUAAG      60

UAGCUACUAU AGUCUAGACG GCCAGAGGG                                        89
```

(2) INFORMATION FOR SEQ ID NO:3:

(i) SEQUENCE CHARACTERISTICS:
        (A) LENGTH:20 bases         (B) TYPE:nucleic acid         (C) STRANDEDNESS:single stranded         (D) TOPOLOGY:linear     (ix) FEATURE:
        (A) NAME/KEY:RT Primer         (D) OTHER INFORMATION:

(ix) SEQUENCE DESCRIPTION:SEQ ID NO:3:

```
TGCCTGCAGG TCGACTCTAG                                                  20
```

(2) INFORMATION FOR SEQ ID NO:4:

(i) SEQUENCE CHARACTERISTICS:
        (A) LENGTH:89 bases         (B) TYPE:nucleic acid         (C) STRANDEDNESS:single stranded         (D) TOPOLOGY:linear     (ix) FEATURE:
        (D) OTHER INFORMATION:

(ix) SEQUENCE DESCRIPTION:SEQ ID NO:4:

```
GACUUCGAAC GUACGGACGU CCAGCUGAGA UCUCCUAGGG GCCCAUGGCU CGAGCUUAAG      60

UAGCUACUAU AGUCUAGACG GCCAGAGGG                                        89
```

(2) INFORMATION FOR SEQ ID NO:5:

(i) SEQUENCE CHARACTERISTICS:
        (A) LENGTH:78 bases         (B) TYPE:nucleic acid         (C) STRANDEDNESS:single stranded         (D) TOPOLOGY:linear

```
    (ix) FEATURE:
         (D) OTHER INFORMATION:

(ix) SEQUENCE DESCRIPTION:SEQ ID NO:5:

TGCCTGCAGG TCGACTCTAG AGGATCCCCG GGTACCGAGC TCGAATTCAT CGATGATATC      60

AGATCTCGCC GGTCTCCC                                                    78

(2) INFORMATION FOR SEQ ID NO:6:

(i) SEQUENCE CHARACTERISTICS:
         (A) LENGTH:77 bases (B) TYPE:nucleic acid (C) STRANDEDNESS:single stranded (D) TOPOLOGY:linear (ix) FEATURE:
         (D) OTHER INFORMATION:

(ix) SEQUENCE DESCRIPTION:SEQ ID NO:6:

TGCCTGCAGG TCGACTCTAG AGGATCCCCG GGTACCGAGC TCGAATTCAT CGATGATATC      60

AGATCTGCCG GTCTCCC                                                     77

(2) INFORMATION FOR SEQ ID NO:7:

(i) SEQUENCE CHARACTERISTICS:
         (A) LENGTH:20 bases (B) TYPE:nucleic acid (C) STRANDEDNESS:single stranded (D) TOPOLOGY:linear (ix) FEATURE:
         (A) NAME/KEY:Oligonucleotide probe biotinylated at 5' position
         (D) OTHER INFORMATION:

(ix) SEQUENCE DESCRIPTION:SEQ ID NO:7:

GATGAATTCG AGCTCGGTAC                                                  20

(2) INFORMATION FOR SEQ ID NO:8:

(i) SEQUENCE CHARACTERISTICS:
         (A) LENGTH:20 bases (B) TYPE:nucleic acid (C) STRANDEDNESS:single stranded (D) TOPOLOGY:linear (ix) FEATURE:
         (A) NAME/KEY:Oligonucleotide probe biotinylated at 5' position
         (D) OTHER INFORMATION:

(ix) SEQUENCE DESCRIPTION:SEQ ID NO:8:

GAGACCGGCA GATCTGATAT                                                  20
```

(2) INFORMATION FOR SEQ ID NO:9:

(i) SEQUENCE CHARACTERISTICS:
        (A) LENGTH:89 bases         (B) TYPE:nucleic acid         (C) STRANDEDNESS:single stranded         (D) TOPOLOGY:linear     (ix) FEATURE:
        (A) NAME/KEY:Template RNA         (D) OTHER INFORMATION:

(ix) SEQUENCE DESCRIPTION:SEQ ID NO:9:

```
GGGAGACCGG CAGAUCUGAU AUCAUCGAUG AAUUCGAGCU CGGUACCCGG GGAUCCUCUA      60

GAGUCGACCU GCAGGCAUGC AAGCUUCAG                                       89
```

(2) INFORMATION FOR SEQ ID NO:10:

(i) SEQUENCE CHARACTERISTICS:
        (A) LENGTH:20 bases         (B) TYPE:nucleic acid         (C) STRANDEDNESS:single stranded         (D) TOPOLOGY:linear     (ix) FEATURE:
        (D) OTHER INFORMATION:

(ix) SEQUENCE DESCRIPTION:SEQ ID NO:10:

```
TGCCTGCAGG TCGACTCTAG                                                 20
```

(2) INFORMATION FOR SEQ ID NO:11:

(i) SEQUENCE CHARACTERISTICS:
        (A) LENGTH:20 bases         (B) TYPE:nucleic acid         (C) STRANDEDNESS:single stranded         (D) TOPOLOGY:linear     (ix) FEATURE:
        (A) NAME/KEY:Oligonucleotide probe biotinylated at 5'
            position
        (D) OTHER INFORMATION:

(ix) SEQUENCE DESCRIPTION:SEQ ID NO:11:

```
GATGAATTCG AGCTCGGTAC                                                 20
```

(2) INFORMATION FOR SEQ ID NO:12:

(i) SEQUENCE CHARACTERISTICS:
        (A) LENGTH:20 bases         (B) TYPE:nucleic acid         (C) STRANDEDNESS:single stranded         (D) TOPOLOGY:linear

```
    (ix) FEATURE:
         (A) NAME/KEY:Oligonucleotide probe labeled with HRP at 5'
             position
         (D) OTHER INFORMATION:

(ix) SEQUENCE DESCRIPTION:SEQ ID NO:12:

GAGACCGGCA GATCTGATAT                                                    20
```

DETECTION OF REVERSE TRANSCRIPTASE BY DNA HYBRIDIZATION ASSAY

CROSS-REFERENCE TO RELATED APPLICATION

This application is a continuation-in-part of U.S. Ser. No. 07/821,512 filed Jan. 15, 1992 which is now abandonded.

FIELD OF THE INVENTION

This invention is related to the detection of reverse transcriptase and, more specifically, to the following: a) detection of such enzymes by allowing expression of their enzymatic activity followed by the detection of the resulting DNA; b) identification of drug-resistant reverse transcriptase mutants in samples; and/or c) screening of compounds for reverse transcriptase inhibitory activity.

BACKGROUND OF THE INVENTION

Retroviruses are enveloped viruses with a single stranded RNA genome in which the virion contains a reverse transcriptase (RT) enzyme essential for viral replication. All known reverse transcriptases are multifunctional with three different enzymatic activities: RNA-dependent DNA polymerase, RNase H, and DNA-dependent DNA polymerase. During retroviral replication, the first one of these, RNA-dependent DNA polymerase activity, generates a DNA (cDNA) strand complementary to the viral RNA. This first step is followed by the degradation of the original viral RNA strand by RNase H and then the DNA-dependent DNA polymerase activity helps generating a second DNA strand complementary to the first. This double stranded DNA is then integrated into the host genome leading to the ultimate replication of the virus.

Since the original discovery of reverse transcriptase in 1970, and in recognition of its important role, RT is frequently measured as an indication of the presence of a retrovirus. Detection of RT can be very important because this enzyme is a logical target for anti-viral therapy and, therefore, anti-viral drug screening can be carried out by RT detection.

One of the challenges facing clinicians in using anti-viral agents to treat patients is the development of mutant viruses resistant to those antivirals. The problem is especially acute in the development of anti-HIV agents. HIV is the causative agent of AIDS.

Thus, it is also important to clinicians to have the ability to determine whether RT in a clinical isolate is resistant and to what level to a particular drug or drugs.

RT can be detected directly as by the detection of certain viruses or indirectly by the detection of certain nucleic acids. One current method for detecting RT includes the use of a poly (rA) template and an oligo (dT) primer, approximately 15–20 nucleotides long, in presence of tritiated TTP ($^3$H-TTP). After the formation of the template primer complex, primer extension is carried out in the presence of tritiated TTP followed by cold trichloroacetic acid precipitation of the DNA and RNA. Then, after a centrifugation or filtration and wash steps, scintillation counter measurement of the resuspended pellet, to determine the presence and the amount of incorporated $^3$H-TTP, provides an indication of the presence of RT in the original sample. An alternative to this method is the use of $^{32}$P-TTP, instead of $^3$H-TTP. One such test is described by Krug et al., Meth. Enz., Vol. 152, 316 (1987).

Yet another alternative method for the measurement of RT is described in EP 0 392 459, published Oct. 17, 1990. This European patent application discloses a method for the determination of the presence of RT in which an artificially prepared adenine ribopolynucleotide RNA template and an oligodeoxythyminenucleotide primer are reacted with a biotinylated deoxyuridine triphosphate in the presence of a sample. After separation of the product from unreacted biotinylated reagent, the amount of incorporated biotin is measured.

The VII International Conference on AIDS, Abstract No. M.A. 1084, Jun. 16–21, 1991, describes an ELISA for measuring RT activity which involves using biotin and dioxigenin labeled nucleotides. The polymerization product is immobilized on a streptavidin-coated microtiter plate via the biotin/streptavidin interaction. RT activity is measured using a peroxidase-labeled anti-dioxigenin antibody which binds to dioxigenin-labeled cDNA.

Similarly, Konig et al., Journal of Cellular Biochemistry, Keystone Symposia on Molecular and Cellular Biology, Supplement 16E, Mar. 27–Apr. 4, 1992, Abstract No. Q222, describes a reverse transcriptase assay using biotin and dioxigenin as described above to screen compounds for activity as reverse transcriptase inhibitors.

These methods for RT detection are in general tedious, time consuming and, in most instances, generate hazardous waste. Additionally, such methods are not entirely specific because the non-reverse transcriptases may also generate a DNA duplex when the substrate (template) utilized is a homopolymer.

There exists a need for a convenient and rapid method for RT detection without generating hazardous wastes. There also exists a need to evaluate whether reverse transcriptase in a sample is resistant to any reverse transcriptase inhibitor (s) and to screen compounds for activity as reverse transcriptase inhibitors.

SUMMARY OF THE INVENTION

In one embodiment this invention concerns a method for detecting reverse transcriptase in a sample suspected of containing reverse transcriptase comprising the steps of:

(A) incubating a synthetic heteropolymeric RNA template molecule containing 40–500 nucleotides with an oligonucleotide primer complementary to a portion of said RNA molecule and of sufficient length to form a stable template-primer complex;

(B) contacting the complex formed in step (A) with a sample suspected of containing reverse transcriptase under conditions leading to the production of a cDNA strand complementary to the template RNA and hybridized thereto if reverse transcriptase was present;

(C) degrading the RNA template from the RNA-cDNA complex formed in step (B) resulting in single stranded cDNA;

(D) hybridizing said cDNA with a chemically modified oligonucleotide probe or probes to permit capture and/or detection of the cDNA-probe complex formed;

(E) separating the cDNA-probe complex formed in step (D) from unreacted probe, wherein steps (D) and (E) can be carried out sequentially or simultaneously; and (F) detecting a label in a labeled cDNA complex, wherein said label is introduced into said complex from labeled oligonucleotide primer, labeled oligonucleotide probe or a labeled third oligonucleotide when the primer is unmodified.

In the methods described herein, the oligonucleotide primer can have one of the following three formats: first, it can be a labeled oligonucleotide, in which case the chemically modified oligonucleotide is an oligonucleotide to which is attached a capture hapten; second, an oligonucleotide with an attached capture hapten in which case the chemically modified oligonucleotide is the labeled oligonucleotide; and third, an unlabeled oligonucleotide in which case the assay contains both an oligonucleotide with an attached capture hapten and a labeled oligonucleotide.

In a second embodiment, this invention concerns a method for detecting and/or quantitating drug resistance of reverse transcriptase in a sample which comprises:

(A) incubating a synthetic heteropolymeric RNA template molecule containing 40–500 nucleotides with an oligonucleotide primer complementary to a portion of said RNA molecule and of sufficient length to form a stable template-primer complex;

(B) contacting the complex formed in step (A) with a sample containing reverse transcriptase and at least one drug known to have reverse transcriptase inhibitory activity under conditions leading to the production of a cDNA strand complementary to the template RNA and hybridized thereto if the reverse transcriptase was not inhibited by the drug;

(C) degrading the RNA template from the RNA-cDNA complex if formed in step (B) resulting in single stranded cDNA;

(D) hybridizing said cDNA if formed with a chemically modified oligonucleotide probe or probes to permit capture and/or detection of the cDNA-probe complex formed;

(E) separating the cDNA-probe complex if formed in step (D) from unreacted probe, wherein steps (D) and (E) can be carried out sequentially or simultaneously; and (F) detecting and/or quantitating a label in a labeled cDNA complex, wherein said label is introduced into said complex from labeled oligonucleotide primer, labeled oligonucleotide probe or a labeled third oligonucleotide when the primer is unmodified, and further wherein the amount of label is a measure of the resistance of the reverse transcriptase to the drug or drugs evaluated at the concentration tested.

In a third embodiment, this invention concerns a method for detecting and/or quantitating reverse transcriptase inhibitory activity of a compound which comprises:

(A) incubating a synthetic heteropolymeric RNA template molecule containing 40–500 nucleotides with an oligonucleotide primer complementary to a portion of said RNA molecule and of sufficient length to form a stable template-primer complex;

(B) contacting the complex formed in step (A) with an appropriate reverse transcriptase standard and at least one compound suspected to be a reverse transcriptase inhibitor under conditions leading to the production of a cDNA strand complementary to the template RNA and hybridized thereto if the reverse transcriptase was not inhibited by the drug;

(C) degrading the RNA template from the RNA-cDNA complex if formed in the presence of the compound in step (B) resulting in single stranded cDNA;

(D) hybridizing said cDNA if formed in the presence of the compound with a chemically modified oligonucleotide probe or probes to permit capture and/or detection of the cDNA-probe complex formed;

(E) separating the cDNA-probe complex if formed in the presence of the compound in step (D) from unreacted prober wherein steps (D) and (E) can be carried out sequentially or simultaneously; and (F) detecting and/or quantitating a label in a labeled cDNA complex, wherein said label is introduced into said complex from labeled oligonucleotide primer, labeled oligonucleotide probe or a labeled third oligonucleotide when the primer is unmodified; and further wherein the amount of label is a measure of the ability of the compound or compounds evaluated to inhibit reverse transcriptase activity at the concentration tested.

DETAILED DESCRIPTION OF THE INVENTION

In one embodiment this invention concerns a method for detecting RT in a sample suspected of containing RT. This method depends on the enzymatic activity of RT. If present in a sample suspected of containing the enzyme, it can act as a polymerase for the primer extension reaction utilizing an RNA template and a primer in presence of the appropriate dNTPs to form a duplex. One of the strands of this duplex is RNA and the second strand is a synthetic cDNA. Synthetic cDNA can then be obtained by degrading RNA from the duplex. During the degradation of RNA from the duplex, all other RNA present is also degraded. Following degradation of RNA, the synthesized single-stranded cDNA can be hybridized with a chemically modified, labeled probe and then separated from unhybridized matter. The single-stranded cDNA can also be hybridized with a probe chemically modified with a capture hapten. In such an assay format, detectable label can be introduced into the RNA-cDNA duplex by initially utilizing labeled primer or, if unmodified primer is used, utilizing a labeled third oligonucleotide. Subsequent detection of the label is a confirmation that cDNA was in fact formed, catalyzed by RT; that is, RT was present in the sample.

In a second embodiment this invention concerns a method for detecting and/or quantitating drug resistance of RT in a sample containing RT which comprises (A) incubating a synthetic heteropolymeric RNA template molecule containing 40–500 nucleotides with an oligonucleotide primer complementary to a portion of said RNA molecule and of sufficient length to form a stable template-primer complex;

(B) contacting the complex formed in step (A) with a sample containing reverse transcriptase and at least one drug known to have reverse transcriptase inhibitory activity under conditions leading to the production of a cDNA strand complementary to the template RNA and hybridized thereto if the reverse transcriptase was not inhibited by the drug;

(C) degrading the RNA template from the RNA-cDNA complex if formed in step (B) resulting in single stranded cDNA;

(D) hybridizing said cDNA if formed with a chemically modified oligonucleotide probe or probes to permit capture and/or detection of the cDNA-probe complex formed;

(E) separating the cDNA-probe complex if formed in step (D) from unreacted probe, wherein steps (D) and (E) can be carried out sequentially or simultaneously; and (F) detecting and/or quantitating a label in a labeled cDNA complex, wherein said label is introduced into said complex from labeled oligonucleotide primer, labeled oligonucleotide probe or a labeled third oligonucleotide when the primer is unmodified, and further wherein the amount of label is a measure of the resistance of the reverse transcriptase to the drug or drugs evaluated to the concentration tested. Thus, if the amount of label is at the same level as a "no drug" control, then it indicates that the RT in the sample is resistant to the drug or drugs evaluated at the concentration tested. If the amount of label is less than that with a "no drug" control, then this indicates the level of resistance and if no label is detected, then this indicates that the reverse transcriptase is not resistant to the drug or drugs evaluated at the concentration tested.

The ability to screen for drug resistant RT mutants is important because one of the challenges facing the therapeutic application of anti-viral agents, as was noted above, is the development of mutant viruses resistant to those antivirals. The problem is especially acute in the development of anti-HIV agents. HIV is the causative agent of AIDS.

For example, the drugs currently approved by the FDA for use in treatment of AIDS (AZT, ddI, and ddC) are all nucleoside analogs. On entering cells, each drug is metabolized to the nucleotide triphosphate, which is the active form, i.e., the form in which the drug inhibits RT activity in vivo. When incorporated into a replicating DNA strand, the drugs cause premature chain termination. Thus, the mode of action of all three drugs is the inhibition of RT activity.

There is also a class of drugs which are non-nucleoside analogs useful for inhibiting RT activity. The non-nucleoside analogs do not need to be converted to an active form because they are already in their active form.

It is known that viral isolates from patients on long-term continuous therapy with these drugs show mutations at certain codons in the RT gene which have been shown to affect the resistance of the RT to the various drugs. For example, substitution of phenylalanine or tyrosine for the wild-type threonine at codon 215, and/or glutamine for the wild-type lysine at codon 219 leads to resistance to AZT, whereas substitution of valine for the wild-type leucine at codon 74 leads to ddI resistance. See Larder, B. A. and Kemp, S. D. Multiple mutations in HIV-1 reverse transcriptase confer high-level resistance to zidovudine (AZT). Science 246:1155–1158 (1989); and St. Clair, M. H., Martin, J. L., Tudor-Williams, G., Bach, M. C., Vavro, C. L., King, D. M., Kellam, P., Kemp, S. D., and Larder, B. A. Resistance to ddI and sensitivity to AZT induced by a mutation in HIV-1 reverse transcriptase. Science 253:1557–1559 (1991).

In a third embodiment, this invention concerns a method for evaluating the reverse transcriptase inhibitory activity of a compound which comprises (A) incubating a synthetic heteropolymeric RNA template molecule containing 40–500 nucleotides with an oligonucleotide primer complementary to a portion of said RNA molecule and of sufficient length to form a stable template-primer complex;

(B) contacting the complex formed in step (A) with an appropriate reverse transcriptase standard and at least one compound suspected to be a reverse transcriptase inhibitor under conditions leading to the production of a cDNA strand complementary to the template RNA and hybridized thereto if the reverse transcriptase was not inhibited by the drug;

(C) degrading the RNA template from the RNA-cDNA complex if formed in the presence of the compound in step (B) resulting in single stranded cDNA;

(D) hybridizing said cDNA if formed in the presence of the compound with a chemically modified oligonucleotide probe or probes to permit capture and/or detection of the cDNA-probe complex formed;

(E) separating the cDNA-probe complex if formed in the presence of the compound in step (D) from unreacted probe, wherein steps (D) and (E) can be carried out sequentially or simultaneously; and (F) detecting and/or quantitating a label in a labeled cDNA complex, wherein said label is introduced into said complex from labeled oligonucleotide primer, labeled oligonucleotide probe or a labeled third oligonucleotide when the primer is unmodified; and further wherein the amount of label is a measure of the ability of the compound or compounds evaluated to inhibit reverse transcriptase activity at the concentration tested.

Thus, if the amount of label is at the same level as the "no compound" control, then it indicates that the compound is not a reverse transcriptase inhibitor and if the amount of label is less than that found with a "no compound" control, then this indicates the degree to which the compound inhibits reverse transcriptase activity at the concentration tested and if no label is detected, then this indicates inhibition of reverse transcriptase activity at the concentration tested.

For example, the drugs mentioned above in connection with treatment of AIDS were discovered through their ability to inhibit the growth of HIV in cultured cells.

In the past, it has not been possible to demonstrate drug resistance by direct assay of the RT due to limitations of the current methods for measuring RT. The usual method for measuring reverse transcriptase is the incorporation of radio-actively labeled thymidine into acid-precipitable material in the presence of a poly (rA) template and an oligo (dT) primer. Use of a homopolymeric template restricts the utility of RT assays in evaluating and testing for resistance to nucleoside inhibitors, because different templates must be used for different analogs and reverse transcriptases have a strong preference for poly (rA) among the possible homopolymeric templates. In addition, the method is tedious, time-consuming and inconvenient to perform, produces radioactive and other hazardous waste, and can be inaccurate if not carefully standardized and controlled by the individual laboratory.

Since the method of the invention employs a heteropolymeric template, the same template can be used to test inhibition by any nucleoside analog. However, before testing, the nucleoside analog must be converted to its corresponding active phosphorylated form, i.e., the form in which it is active in vivo as was discussed above. It may be helpful to consider nucleoside analogs as prodrugs or zymogens which require further physiological processing to convert a prodrug to a drug or a zymogen to an active enzyme. In contrast, non-nucleoside analogs need not undergo any conversion because they are in their active form when administered. In other words, non-nucleoside analogs need no further physiological processing in order to inhibit RT activity.

Thus, the ability to demonstrate RT inhibition by a compound by directly testing the effect on RT activity can be accomplished using the method of the instant invention.

One type of RNA template which can be utilized in the method of this invention is a synthetic RNA, having no relationship to the RNA of a virus which may also be present in a sample, and which meets various criteria for the convenience of the subsequent primer hybridization and primer extension reactions. One such template RNA has a base sequence containing 89 bases and is shown below:

```
5'-GGGAG ACCGG CAGAU CUGAU AUCAU CGAUG AAUUC GAGCU CGGUA   SEQ ID NO:1:

CCCGG GGAUC CUCUA GAGUC GACCU GCAGG CAUGC AAGCU UCAG-3'
```

This sequence represents a portion of the multiple cloning site from plasmid pSP72, a plasmid which is commercially available (Promega). This plasmid is described in Krieg et al., Methods in Enzymology, Vol. 155, 397–415 (1987), "In Vitro RNA Synthesis with SP6 RNA Polymerase". This particular sequence has several advantages over other possible RNA sequences: First, it has multiple cloning sites which permit a relatively convenient synthesis of significant practical quantities of RNA. Second, the template sequence contains only 55% GC. Because most restriction enzymes recognize GC-rich sequences, most multiple cloning sites are also rich in GC. Use of this method of RNA preparation with such sites would otherwise lead to RNA with high GC content. In turn, such RNA can lead to abnormal hybridization results. Third, this sequence is also not palindromic or repetitive which could lead to abnormal RNA production. Fourth, a cleavage site for Pvu II is favorably located in pSP72 so as to produce the short (89 bases) RNA. This leads to a more sensitive assay because only one label can be incorporated for each cDNA product strand. Therefore, the shorter the RNA template, the more labels can be incorporated per unit cDNA synthesized. Finally, Pvu II produces a blunt-ended cut which is important to avoid defective RNA sequence synthesis. If one were to start without a blunt-ended nucleic acid, production of such blunt-end would require an extra step.

For retroviral samples where both RNA and reverse transcriptase can be present, the endogenous RNA of the virus can serve as a template when using a primer specific for an appropriate region of the RNA. In such an assay format, extension by endogenous RT and carrying out the assay can afford a second level of affirmation as to the presence of RT in the sample and a confirmation of the viral RNA sequence for which the primer was chosen.

The present invention can also be used to identify the viral source of the RT. Such identification can be predicated upon the known specificity of RT for its natural primer. When assaying RT using a synthetic homopolymer and its corresponding primer, the addition of the natural primer to the reaction is known to inhibit reverse transcription. Because the natural primer is different for different viruses, the type of RT in a reaction can be determined by finding inhibition by the appropriate natural primer sequence. A panel of such sequences or transfer RNAs (tRNAs) then allows the identification of the viral source of the RT in a sample.

This type of inhibition results from the preference of the enzyme for its natural primer as compared to the primer for the synthetic homopolymer. For example, for HIV-1 RT, lysine tRNA acted as an inhibitor while valine tRNA did not inhibit the reaction. See Barat et al., Nucleic Acids Research, Vol. 19, 751–757 (1991) and Bordier et al., Nucleic Acids Research, Vol. 18, 429–436 (1990).

In general, the template RNA should have approximately 40 to approximately 500 bases. Higher number of bases can lead to loss of sensitivity of the assay.

The types of primers that can be utilized are oligonucleotides which can be unmodified or chemically modified to contain a ligand that can be subsequently detected (by the addition of a binder specific for the ligand, when the ligand is a label, conjugated to an appropriate detector) or used as part of a ligand-binder pair, when the ligand is a capture hapten, for capture. The primer must be highly specific for the intended target sequence without base-pairing to other regions within the target molecule, be non-self complementary (that is, not form dimers or hairpins) and form stable duplexes with the template under the appropriate conditions.

Stability in this context refers to resistance to disruption by the template-primer hybridization conditions. Typically, one can perform the hybridization step at 5–10° C. below the melting temperature ($T_m$) of the desired product, so that non-specific hybrids are disrupted, but not the specific ones. $T_m$ can be calculated according to nearest-neighbor thermodynamic values. For example, see Breslauer et al., Proc. Nat. Acad. Sci., Vol. 83, 3746–3750 (1986).

An example of a preferred primer is 3'-TGCCT GCAGG TCGAC TCTAG-5'. This primer forms the following complex with the 89-base RNA template:

```
3' G ACUUC GAACG UACGG ACGUC CAGCU GAGAU CUCCU AGGGG CCCAU
                 5'    TGCC TGCAG GTCGA CTCTA G   3'  SEQ ID NO:3:
                              RT Primer

- GGCUC GAGCU UAAGU AGCUA CUAUA GUCUA GACGG CCAGA GGG 4'   SEQ ID NO:2:
```

In turn, this complex is primer-extended with RT, if present, to the following RNA-cDNA complex:

```
3' G ACUUC GAACG UACGG ACGUC CAGCU GAGAU CUCCU AGGGG CCCAU -

5'    TGCC TGCAG GTCGA CTCTA GAGGA TCCCC GGGTA -
                       RT Primer
```

-continued

```
-GGCUC GAGCU UAAGU AGCUA CUAUA GUCUA GACGG CCAGA GGG 5'    SEQ ID NO:4:

-CCGAG CTCGA ATTCA TCGAT GATAT CAGAT CTGCC GGTCT CCC 3'    SEQ ID NO:5:
```

Degradation of the RNA from the above complex leads to the following DNA:

for optimum activity and, thus, they may differ in their response to a compound or compounds.

```
5' TGCC TGCAG GTCGA CTCTA GAGGA TCCCC GGGTA CCGAG CTCGA- SEQ ID NO:6:
         RT Primer
ATTCA TCGAT GATAT CAGAT CTGCC GGTCT CCC 3'
```

The natural template for RT is a heteropolymeric RNA molecule, but methods commonly used to measure RT employ homopolymeric templates. This entails a loss of specificity because, while no normal mammalian cellular DNA polymerase has been shown to copy the heteropolymeric portions of a natural RNA, some (especially DNA polymerase gamma) are capable of transcribing poly (rA). Thus, reactivity in a homopolymeric template assay system does not conclusively show that the activity is due to the presence of a reverse transcriptase. Because these other enzymes do not work with heteropolymeric template molecules, use of such a template ensures reactivity only with RT.

The primer to template ratio is not critical and a ratio of 0.6–200:1 can be utilized. It is preferred that this ratio be 1–1.5:1.

The template-primer complex formed (i) is contacted with sample suspected of containing reverse transcriptase under conditions leading to the production of a cDNA strand complementary to the template RNA and hybridized thereto if reverse transcriptase was present when detecting reverse transcriptase in a sample suspected of containing reverse transcriptase; (ii) is contacted with sample containing reverse transcriptase and with at least one drug known to inhibit reverse transcriptase activity when trying to detect and/or quantitate drug resistance of reverse transcriptase in a sample under conditions leading to the production of a cDNA strand complementary to the template RNA and hybridized thereto if reverse transcriptase was not inhibited by the drug; or (iii) is contacted with an appropriate reverse transcriptase standard in the presence and absence of the compound suspected to be a reverse transcriptase inhibitor under conditions leading to the production of a cDNA strand complementary to the template RNA and hybridized thereto if reverse transcriptase was not inhibited by the compound.

When screening for drug resistance of reverse transcriptase, any drug or drugs known to be reverse transcriptase inhibitors can be used provided that they are added in their active form or are converted to their active form prior to use in the assay of the present invention. This is necessary because as is discussed above, this is an in vitro assay, and, thus, the drug will not be physiologically processed to its active form as would occur in an in vivo system.

When screening a compound or compounds for activity as a potential reverse transcriptase inhibitor, in addition to adding the compound or compounds to be evaluated, an appropriate reverse transcriptase standard should also be used. By appropriate reverse transcriptase standard it is meant that the compound or compounds which are expected to inhibit RT activity from a virus should be evaluated using that particular RT (i.e., the appropriate RT standard) because RTs from various sources differ in the conditions required for optimum activity and, thus, they may differ in their response to a compound or compounds.

Following primer extension, if RT is present, and degradation of RNA, including RNA from the RNA-cDNA duplex generated during the RT-catalyzed primer extension, the single-stranded cDNA thus formed can be detected by the assay of this invention.

The oligonucleotide probes utilized in the assays of this invention can be used for purposes of capture and/or detection of the cDNA-probe complex formed in the hybridization step between cDNA and such a probe.

Oligonucleotide probes to be used as detection reagents can be chemically modified to have a detectable moiety directly attached to the probe before hybridization, or the probes can be chemically modified to include a ligand to permit subsequent detection by the addition of a binder specific for that ligand, conjugated to an appropriate detector.

Oligonucleotides designed as capture probes can be unmodified or chemically modified with a ligand to permit subsequent complexation to a binder specific for that ligand. Unmodified capture probes are utilized for this purpose by hybridization capture to a complementary strand immobilized on a solid support such as a microplate, bead or tube. For purposes of separating the cDNA-probe complex from unreacted probes, the cDNA-probe complexes can be captured by a binder attached to a solid support.

If separate capture and detector oligonucleotide probes are used, their sequences must be chosen so as not to be complementary to each other and they must react with different sites on the target sequence.

Examples of preferred probes are:

```
5'-GATGA ATTCG AGCTC GGTAC-3'        SEQ ID NO:7:
   |
   biotin

5'-GAGAC CGGCA GATCT GATAT-3'        SEQ ID NO:8:
   |
   HRP
```

Examples of ligand-binder pairs include biotin-avidin, biotin-streptavidin and fluorescein-antifluorescein.

General reaction conditions for the primer extension and hybridization reactions are well known. For the primer extension reaction with RT, reaction conditions vary with the nature of the RT present. A large variety of reaction conditions has been published. A representative sample of reaction conditions along with a reference are provided below:

| RT Type[1] | Formulation | | Reference[2] |
|---|---|---|---|
| AMV | 50 mM | Tris, pH 8.3 | 1 |
| | 50 mM | KCl | |
| | 10 mM | MgCl$_2$ | |
| | 1 mM | EDTA | |
| | 10 µg/mL | BSA | |
| | 1 mM | DTT | |
| HIV-1 & 2 | 40 mM | Tris, pH 7.8 | 2 |
| | 45 mM | KCl | |
| | 10 mM | MgCl$_2$ | |
| | 4 mM | DTT | |
| SIV | 50 mM | Tris, pH 8.0 | 3 |
| | 80 mM | KCl | |
| | 10 mM | MgCl$_2$ | |
| | 0.05% | NP-40 | |
| | 1 mM | DTT | |
| MuLV | 50 mM | Tris, pH 8.3 | 1 |
| | 75 mM | KCl | |
| | 3 mM | MgCl$_2$ | |
| | 100 µg/mL | BSA | |
| | 10 mM | DTT | |
| RMLV | 50 mM | Tris, pH 8.2 | 4 |
| | 50 mM | KCl | |
| | 0.5 mM | MgCl$_2$ | |
| | 0.05% | Triton X-100 | |
| | 1 mM | DTT | |
| EIAV | 50 mM | Tris, pH 7.9 | 5 |
| | 50 mM | KCl | |
| | 5 mM | MgCl$_2$ | |
| | 0.05% | NP-40 | |
| | 5 mM | DTT | |
| FLV | 62 mM | Tris, pH 8.3 | 6 |
| | 60 mM | NaCl | |
| | 5 mM | MnCl$_2$ | |
| | 500 µg/mL | BSA | |
| | 2.5 mM | DTT | |
| FIV | 62 mM | Tris, pH 8.3 | 6, 2 |
| | 20 mM | KCl | |
| | 5 mM | MgCl$_2$ | |
| | 500 µg/mL | BSA | |
| | 2.5 mM | DTT | |
| S. cerevisiae | 50 mM | Tris-HCl, pH 8.3 | 7 |
| | 40 mM | KCl | |
| | 0.8 mM | MnCl$_2$ | |
| | 0.02% | NP-40 | |
| | 500 µg/mL | BSA | |
| | 4 mM | DTT | |
| E. coli | 50 mM | Tris, pH 7.5 | 8 |
| | 75 mM | KCl | |
| | 3 mM | MgCl$_2$ | |
| | 10 mM | DTT | |
| H. halobium | 50 mM | NaPO$_4$, pH 7.0 | 9 |
| | 50 mM | KCl | |
| | 5 mM | MgCl$_2$ | |
| | 10% | glycerol | |
| | 50 µg/mL | BSA | |

[1] Abbreviations: AMV = avian myeloma virus; HIV = human immunodeficiency virus; SIV = simian immunodeficiency virus; MuLV = Moloney murine leukernia virus; RMLV = Rauscher murine leukemia virus; EIAV = equine infectious anemia virus; FLV = feline leukemia virus; FIV = feline immunodeficiency virus

[2] References:
1. Krug et al., Meth. Enz., Vol. 152, 316–325 (1987).
2. Poiesz et al., Proc. Natl. Acad. Sci. USA, Vol. 77, 7415–7419 (1980).
3. Manns et al., Nucl. Acids Res., Vol. 19, 533–537 (1991).
4. Roberts et al., J. Gen. Virol., Vol. 72, 299–305 (1991).
5. Borroto-Esoda et al., J. Virol., Vol. 65, 1952–1959 (1991).
6. Pedersen et al., Science, Vol. 235, 790–793 (1987).
7. Halbreich, Biochemistry International, Vol. 22, 859–866 (1990).
8. Lim et al., Cell, Vol. 56, 891–904 (1989).
9. Ben-Mahrez et al., Eur. J. Biochem., Vol. 195, 157–162 (1991).

Generally, a number of components are commonly utilized in the reaction mixture for the extension of a primer along the RNA template. The pH of the reaction mixture and the nature of the divalent cation are important to enzyme activity. Often, RNase inhibitors and other stabilizers [such as dithiothreitol (DTT) or glycerol] can be added to avoid reagent or sample loss due to adventitious addition of RNase or loss of enzymatic activity on storage.

Because reverse transcriptase is located in the core of the virus particle as a complex with viral RNA, samples suspected of containing RT have to be subjected to certain procedures. A common sample processing method comprises pelleting the virus particles by ultracentrifugation or by normal centrifugation after adding polyethylene glycol (PEG) followed by addition of salt and detergent to lyse the particles and release RT. Mild nonionic detergent treatment (0.04–0.1% Triton X-100 or NP-40) is commonly employed.

Within (infected) cells, RT is harder to separate from endogenous DNA polymerases and inhibitors such as proteases and nucleases. Such separations can require high salt (0.5 M KCl) and/or nonionic detergent (for example, 0.5% NP-40) concentrations.

After the formation of the RNA-cDNA complex, it is necessary to degrade the RNA strand from the duplex and, further, it is also necessary to rid the reaction mixture of all RNA to avoid substantial interference with subsequent probe hybridization. This can be accomplished, for example, by the use of any RNase. In general, RNA can be degraded from the duplex by basic hydrolysis which will not degrade DNA, or by enzymatic hydrolysis using, for example, RNaseH. Degradation temperatures are customarily between 25–37° C. The time of such a reaction is usually 5–15 minutes. After the completion of the degradation, if basic hydrolysis was utilized, one customarily adjusts the pH level of the mixture to neutral; by neutral, a pH of 6–8 is acceptable. This is done to avoid subsequent denaturation of labels attached to the oligonucleotide probe, such as enzyme labels and also to avoid DNA/DNA denaturation.

Conditions used for hybridization of probes to cDNA can be selected to maximize the specific binding of the probes to the cDNA and minimize nonspecific binding of these reagents to any other components of the reaction mixture. In general, probes and primers are selected to be at least 17–18 nucleotides in length to allow them to select a unique sequence of DNA in a complex mixture. In one aspect of the assay of the present invention, where a substantially pure, short synthetic RNA template is provided, shorter probes and primers can be used and still have specificity. Formamide can be included as an additive to diminish the formation and strength of undesired hybrids, thereby favoring specificity of the desired reaction. Similarly, temperature and salt concentrations can be important parameters; temperature of hybridization, as described above for primer selection, is based on $T_m$, and can be calculated or measured. Lower salt concentrations can increase stringency. Washes should be brief to avoid dissociation.

Capture of the RT primer extension product cDNA can be achieved by a variety of methods. The initial primer oligonucleotide can be chemically modified to contain a ligand capable of complexing with an immobilized binder. Alternatively, the initial primer oligonucleotide can contain a portion noncomplementary to the RNA template that can subsequently be used to hybridize to an immobilized sequence, the complementary portion of which is available for hybridization. When the initial primer oligonucleotide is unmodified, a separate capture oligonucleotide probe can be used that is chemically modified to contain a ligand capable of complexing with an immobilized binder. Yet another capture method utilizes an antibody/anti-antibody or binder-binder reaction to precipitate the complex product after the ligand-containing chemically modified primer or probe has been previously reacted with a primary binder. Detection of the cDNA-probe complex can be carried out several different ways. The initial primer or a probe can be chemically modified with a ligand (label) to allow subsequent detection through reaction with a binder for the ligand conjugated, for example, to an enzyme, a fluorophore or a chemiluminescent substrate. Alternatively, the probe can be chemically modified directly with a label such as an enzyme, a fluorophore or a chemiluminescent substrate.

EXAMPLE 1

Detection of RT Using Synthetic RNA

I. Reagent Preparation

A. Template RNA

A template RNA was synthesized by in vitro transcription from linearized pSP72 plasmid DNA by performing the following steps:

1. Circular pSP72 plasmid DNA (Promega) was cut with the restriction enzyme Pvu II by overnight incubation at 37° C. of a solution containing 200 μg/mL DNA, 2400 units/mL Pvu II, 6 mM Tris-HCl buffer, pH 7.5, 50 mM NaCl, 6 mM $MgCl_2$, and 1 mM dithiothreitol (DTT).
2. In vitro transcription with T7 RNA polymerase was performed by 2 hour incubation at 37° C. of a solution containing 50 μg/mL of the linearized DNA, 400 units/mL T7 RNA polymerase, 40 mM Tris-HCl buffer, pH 8.0, 6 mM $MgCl_2$, 2 mM spermidine, 10 mM NaCl, 10 mM DTT, 0.5 mM rATP, 0.5 mM rGTP, 0.5 mM rCTP and 0.5 mM rUTP.
3. The DNA was degraded by adding 50 units/mL of RNase-free DNase and incubating 15 minutes at 37° C. The DNase was then inactivated by placing the tube in a boiling water bath for 10 minutes.
4. The RNA was purified by centrifugation using CHROMA SPIN +TE-400 spin columns (Clontech) as follows: the columns were centrifuged twice at 700×g for 3 minutes to remove the buffer they are stored in. 50 μL of RNA-containing solution was added to each column and then centrifuged at 700×g for 5 minutes to remove high molecular weight contaminants. The RNA was then recovered by washing each column with 1 mL of nuclease-free water.

The template RNA produced had the following 89-base sequence:

5'-GGGAG ACCGG CAGAU CUGAU AUCAU CGAUG AAUUC GAGCU CGGUA SEQ ID NO:9:

-CCCGG GGAUC CUCUA GAGUC GACCU GCAGG CAUGC AAGCU UCAG-3'

B. Primer

The following DNA oligonucleotide was synthesized on a DNA synthesizer employing standard methods:

5'-TGCCT GCAGG TCGAC TCTAG-3' SEQ ID NO:10:

C. Probes

The following probe oligonucleotides were synthesized on a DNA synthesizer and conjugated with biotin or horseradish peroxidase (HRP) employing standard methods.

1. Capture Probe (biotin-labeled DNA oligonucleotide)

5'-GATGA ATTCG AGCTC GGTAC-3' SEQ ID NO:11:

```
      |
    biotin
```

2. Detector Probe (HRP-labeled DNA oligonucleotide)

5'-GAGAC CGGCA GATCT GATAT-3' SEQ ID NO:12:
```
      |
     HRP
```

D. Streptavidin-coated Microplates

Plates were coated by adding 0.1 mL of 0.1 M carbonate buffer, pH 9.6, containing 35 μg/mL of streptavidin and incubating at room temperature overnight. After aspiration and washing with PBS, plates were blocked by adding 0.3 mL of PBS, pH 7.4, containing 1.25% BSA and 10% beta-lactose, air-dried and stored with desiccant.

II. Assay

A. Reverse Transcriptase (RT) Reaction

Several RT-catalyzed reactions were carried out using a range (shown in III. Results) of 0.5–1000 munits of recombinant HIV-1 RT (American BioTechnologies, Inc., Cambridge, Mass.). Each concentration of RT was added to give tubes containing 40 μL of the following solution:

| 35 nM | Template RNA |
|---|---|
| 50 nM | Primer |
| 0.5 mM | dATP |
| 0.5 mM | dGTP |
| 0.5 mM | dCTP |
| 0.5 mM | dTTP |
| 1 mM | DTT |
| 40 units | RNasin (RNase inhibitor, Promega) |
| 50 mM | Tris-HCl buffer, pH 8.0 |
| 50 mM | KCl |
| 10 mM | $MgCl_2$ |
| 0.5–1000 mU | Recombinant HIV-1 RT |

These tubes were incubated at 37° C. for 1 hour to allow the synthesis of cDNA.

B. Detection Reaction 1. 10 μL of 1 N KOH was added to each tube and incubated at 37° C. for 15 minutes to hydrolyze the RNA.
2. 10 μL of 1 N $KH_2PO_4$ was added to each tube to neutralize the pH and 50 pL of solution from each tube was transferred to a well of a streptavidin-coated microplate.
3. 50 μL of the following solution was added to each well:

| 10 nM | Capture Probe |
|---|---|
| 10 nM | Detector Probe |
| 0.9 M | Sodium Chloride |
| 0.09 M | Sodium Citrate |
| 10% | Formamide |
| 1.2% | BSA |
| 1.2% | Triton X-100 |

4. The wells were covered with an adhesive plate cover and incubated at 37° C. for 2 hours.
5. The wells were washed 6x with Plate Wash (E. I. du Pont de Nemours and Company, Wilmington, Del.).
6. 100 μL of tetramethylbenzidine (TMB, SOMA) was added to each well and incubated for 1 hour at room temperature.
7. 100 μL of TMB Stop Solution (SOMA) was added to each well and the absorbance (450 nm–650 nm) of the wells was read with a plate reader.

III. Results

| mUnits RT | Absorbance (450 nm–650 nm) |
|---|---|
| 0 | 0.039 |
| 0.5 | 0.109 |
| 1 | 0.229 |
| 2.5 | 0.329 |
| 5 | 0.526 |
| 10 | 0.691 |
| 50 | 1.622 |
| 500 | 2.238 |
| 1000 | 2.401 |

IV. Conclusion

The presence of RT was demonstrated by using its enzymatic activity to generate cDNA which allowed the formation of a sandwich hybrid containing streptavidin, capture probe, cDNA, and detector probe labeled with HRP. The presence of cDNA, and hence RT, was demonstrated by detecting the activity of HRP bound to the sandwich by adding a substrate for HRP. The quantity of cDNA produced was proportional to the amount of RT added.

EXAMPLE 2

Detection and/or Quantitation of Drug Resistance of RT

I. Reagent Preparation

Same as described in Example 1 above.

II. Assay

A. Reverse Transcriptase (RT) Reaction

In this example, RT was obtained from *E. coli* expression systems as described below and was added to each tube in sufficient amount to give a significant signal (about 1–2 absorbance units) in the absence of drug. The same amount of RT was added to each tube. Both a wild-type and a codon 74 (ddI-resistant) mutant RT were tested. Molecular clones were constructed by site-directed mutagenesis to contain a mutation at codon 74, 215, and/or 219. Mutants at codon 74 are resistant to ddI. Wild-type and mutant RT genes of these clones were subcloned into a bacterial expression vector (pKRT2). Bacterial lysates containing recombinant expressed RT, both wild-type and mutant, were made as previously described (D'Aquila, R. T. and Summers, W. C. (1989) JAIDS 2:579–587). The IC50 was determined by computerized estimation (Systat version 5.1) of the median-effect equation: fractional reduction=$1/[1+(IC50/drug\ concentration)^m]$. Each IC50 is the mean of 5–10 experiments. Results of a one-tailed Mann-Whitney U test for the difference between mean wild-type and mutant IC50s: $p<0.005$.

An amount of ddATP (the active form of ddI) varying from 0.0005 to 0.250 mM was added to various tubes containing 40 μL of the following solution:

| | |
|---|---|
| 35 nM | Template RNA |
| 50 nM | Primer |
| 0.5 mM | dATP |
| 0.5 mM | dGTP |
| 0.5 mM | dCTP |
| 0.5 mM | dTTP |
| 1 mM | DTT |
| 40 units | RNasin (RNase inhibitor, Promega) |
| 50 mM | Tris-HCl buffer, pH 8.0 |
| 50 mM | KCl |
| 10 mM | MgCl$_2$ |
| Constant Amt | RT |
| 0.0005–0.250 mM | ddATP |

In this example, the dNTP concentrations were the same as described in Example 1 above.

These tubes were incubated at 37° C. for 1 hour to allow the synthesis of cDNA.

B. Detection Reaction

The detection reaction was the same as described in Example 1 above.

III. Results

Figure 1:
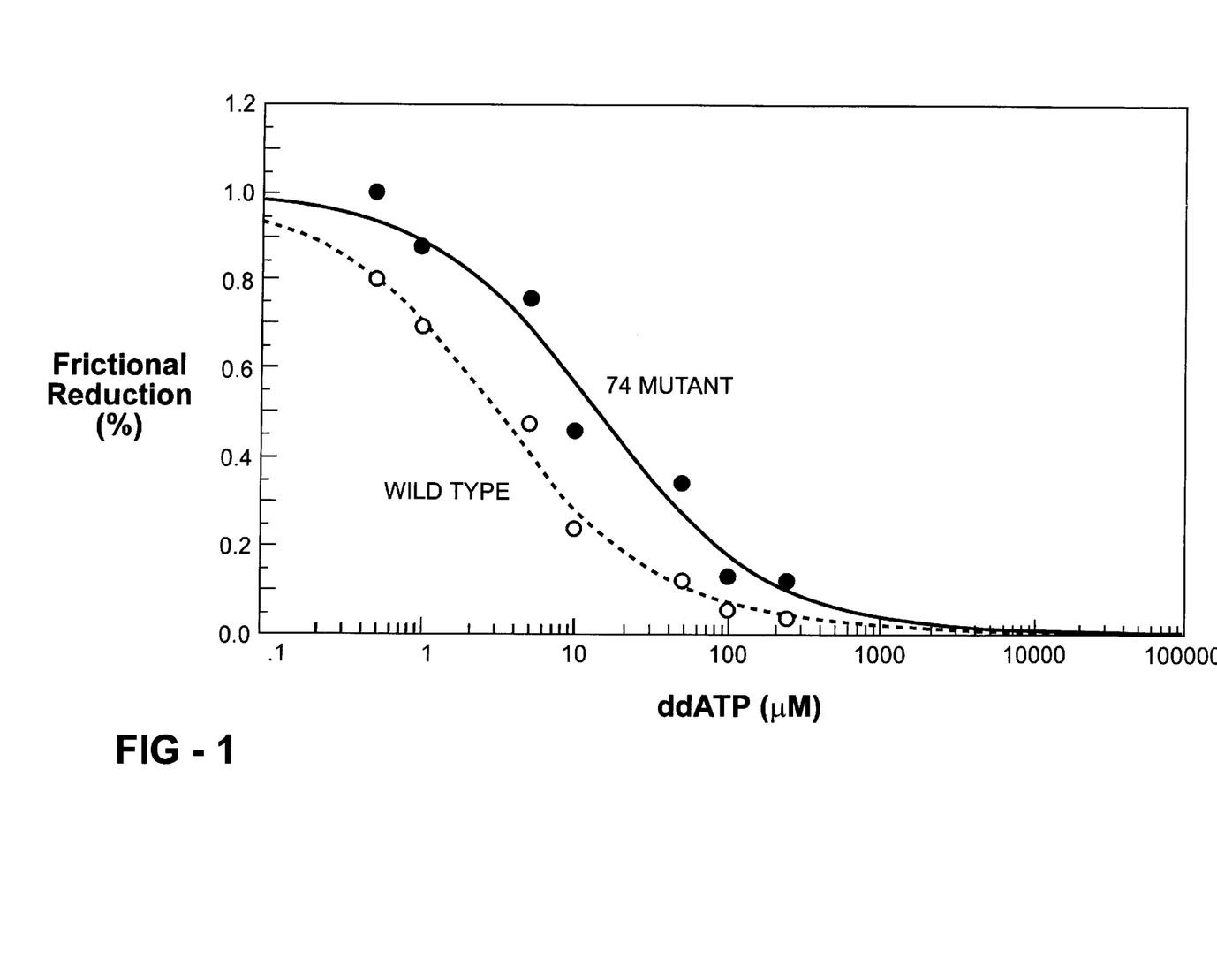
FIG. 1 sets forth data showing the pattern of inhibition observed with *E. coli* wild-type and mutant (ddI resistant) RT.

FIG. 1 shows the pattern of inhibition observed with both the wild-type and the 74 mutant with various amounts of ddATP added to the template-primer complex and sample containing RT. The numerical data summary for the 74 mutant and ddATP, is as follows:

| | Wild-type | Mutant 74 |
|---|---|---|
| # Cases | 10 | 5 |
| Minimum (micromolar) | 3.10 | 11.1 |
| Maximum (micromolar) | 8.70 | 29.4 |
| Mean (IC50) (micromolar) | 6.79 | 16.9 |
| Standard Dev. (micromolar) | 1.84 | 7.26 |

An AZT resistant mutant RT (215/219) and a triple mutant resistant to both ddI and AZT (74/215/219) were made as described above and also tested. The following data was obtained:

| RT | IC50 (multiple determinations, in micromolar) |
|---|---|
| Wild-type | 8.6, 6.7, 7.8, 4.9, 5.7 |
| 74 mutant | 13.2, 16.6, 13.4 |
| 215/219 | 4.6, 5.7, 2.2, 14.6 |
| 74/215/219 | 79.3, 79.3, 41.6, 12.0 |

IV. Conclusion

The drug resistance patterns of RTs carrying various drug resistance mutations as described above were obtained using the method of the instant invention to detect and/or quantitate the level of inhibition. These patterns are depicted in FIG. 1 as noted above.

EXAMPLE 3

Detection and/or Quantitation of Compounds as Potential RT Inhibitors

I. Reagent Preparation

Same as described in Example 1 above.

II. Assay

A. Reverse Transcriptase (RT) Reaction

AMV RT (Du Pont) was used as a model to illustrate use of the method of the present invention for detecting and/or quantitating the ability of a compound to inhibit RT activity. AMV RT was added to give tubes containing 40 μL of the following solution:

| | |
|---|---|
| 35 nM | Template RNA |
| 50 nM | Primer |
| 0.001 mM | dATP |
| 0.001 mM | dGTP |
| 0.001 mM | dCTP |
| 0.001 mM | dTTP |
| 1 mM | DTT |
| 40 units | RNasin ™ (RNase inhibitor, Promega) |
| 50 mM | Tris-HCl buffer, pH 8.0 |
| 50 mM | KCl |
| 10 mM | $MgCl_2$ |
| 200 mU | AMV RT |
| 0–0.010 mM | Inhibitor |

These reaction conditions were similar to those of Example 1 above except with respect to the addition of the inhibitor, the lower dNTP concentration (0.001 mM instead of 0.5 mM) and the increased amount of RT (200 mU instead of 5 mU). Reducing the dNTPs decreases the signal in the assay, but increasing the RT increases the signal. The reduced dNTP concentration helps to make the assay more sensitive to inhibitors which act competitively with the dNTPs and, thus, less inhibitor is needed to achieve the effect. By adding more inhibitor, the same results can be obtained at higher dNTP concentrations.

The tubes were incubated at 37° C. for 1 hour to allow the synthesis of cDNA.

B. Detection Reaction

Same as for Example 1 described above.

III. Results

The dideoxy-versions of all four nucleotides (ddATP, ddTTP, ddCTP, ddGTP) were tested, and all had IC50's between 0.0005 and 0.001 mM, where the expectation would be that an amount equal to the 0.001 mM concentration of the corresponding dNTP should inhibit 50%. A similar experiment showed that inhibition by fosgarnet (a non-nucleoside RT inhibitor) could also be detected and/or quantitated using the method of the present invention. Sample data for ddATP (the active form of ddI) is shown below:

| ddATP (mM) | Absorbance (450 nm–650 nm) |
|---|---|
| 0 | 3.760 |
| 0.0001 | 3.593 |
| 0.00025 | 2.984 |
| 0.0005 | 2.079 |
| 0.0010 | 1.365 |
| 0.0025 | 0.350 |
| 0.0050 | 0.197 |
| 0.0100 | 0.224 |

3.760/2=1.880. The IC50 was between 0.0005 and 0.001 mM.

IV. Conclusion

These data showed that the method of the present invention can be used with a standard RT to test compounds for their ability to inhibit RT activity, i.e., for screening drugs as potential RT inhibitors. To demonstrate the inhibitory effect of dideoxynucleoside inhibitors, the addition of the phosphorylated active forms of the drugs was required; for example, ddATP is the active form of ddI. The method of the instant invention provides a more efficient, less tedious alternative in contrast to methods currently available. For example, demonstration of ddATP as an RT inhibitor using the homopolymer method is difficult because it requires the use of a template, poly (rU), which is inefficiently used by RTs. These data also showed that the present invention can be used to demonstrate inhibition by non-nucleoside RT inhibitors.

What is claimed is:

1. A method for for detecting reverse transcriptase in a sample suspected of containing reverse transcriptase comprising the steps of:
- (A) incubating a synthetic heteropolymeric RNA template molecule containing 40–500 nucleotides with an oligonucleotide primer complementary to a portion of said RNA molecule and of sufficient length to form a stable template-primer complex;
- (B) contacting the complex formed in step (A) with a sample suspected of containing reverse transcriptase under conditions leading to the production of a cDNA strand complementary to the template RNA and hybridized thereto if reverse transcriptase was present;
- (C) degrading the RNA template from the RNA-cDNA complex formed in step (B) resulting in single stranded cDNA;
- (D) hybridizing said cDNA with a chemically modified oligonucleotide probe or probes to permit capture and/or detection of the cDNA-probe complex formed;
- (E) separating the cDNA-probe complex formed in step (D) from unreacted probe, wherein steps (D) and (E) may be carried out sequentially or simultaneously; and
- (F) detecting the presence of reverse transcriptase by detecting a label in a labeled cDNA complex, wherein said label is introduced into said complex from labeled oligonucleotide primer, labeled oligonucleotide probe or a labeled third oligonucleotide when the primer is unmodified.

2. The method of claim 1 wherein the primer is chemically modified with a capture hapten to permit subsequent capture when the probe is chemically modified with a label to permit subsequent detection.

3. The method of claim 1 wherein the primer is chemically modified with a label to permit subsequent detection when the probe is chemically modified with a capture hapten to permit subsequent capture.

4. The method of claim 1 wherein the primer is an unmodified oligonucleotide when in addition to a chemically modified oligonucleotide probe there is also present a third oligonucleotide which is chemically modified.

5. The method of claim 4 wherein the probe is chemically modified with a label when said third oligonucleotide is modified with a capture hapten.

6. The method of claim 4 wherein the probe is chemically modified with a capture hapten when said third oligonucleotide is modified with a label.

7. A method for detecting reverse transcriptase in a sample suspected of containing a retrovirus comprising the steps of:
- (A) incubating the sample suspected of containing RNA with an oligonucleotide primer complementary to a portion of said RNA molecule and of sufficient length to form a stable template-primer complex;
- (B) further incubating the complex formed in step (A) if RNA was present under conditions leading to the production of a cDNA strand complementary to the template RNA and hybridized thereto catalyzed by reverse transcriptase if present in the sample;
- (C) degrading the RNA template from the RNA-cDNA complex formed in step (B) resulting in single stranded cDNA;
- (D) hybridizing said cDNA with chemically modified oligonucleotide probe or probes to permit capture and/or detection of the cDNA-probe complex formed;
- (E) separating the cDNA-probe complex formed in step (D) from unreacted probe, wherein steps (D) and (E) may be carried out sequentially or simultaneously; and
- (F) detecting the presence of reverse transcriptase by detecting a label in a labeled cDNA complex, wherein said label is introduced into said complex from labeled oligonucleotide primer, labeled oligonucleotide probe or a labeled third oligonucleotide when the primer is unmodified.

* * * * *